United States Patent [19]

Guidoux et al.

[11] Patent Number: 4,970,143
[45] Date of Patent: Nov. 13, 1990

[54] USE OF ACETOACETATE FOR PRESERVATION OF LIVING TISSUE

[75] Inventors: René Guidoux, Lausanne, Switzerland; Olga Gomez, Lidingoe, Sweden

[73] Assignee: Nestec S.A., Vevey, Switzerland

[21] Appl. No.: 896,620

[22] Filed: Aug. 14, 1986

[30] Foreign Application Priority Data

Sep. 6, 1985 [EP] European Pat. Off. ......... 85111290.4

[51] Int. Cl.$^5$ .......................... A01N 1/02; C23F 11/18
[52] U.S. Cl. ........................................ 435/1; 435/283; 435/240.1; 422/1; 422/17
[58] Field of Search ................ 435/1, 283, 240, 240.1; 62/62, 78, 440; 422/1, 17

[56] References Cited

U.S. PATENT DOCUMENTS

| | | | |
|---|---|---|---|
| 4,494,385 | 1/1985 | Kuraoka et al. | 435/1 |
| 4,663,166 | 5/1987 | Veech | 424/146 |
| 4,663,289 | 5/1987 | Veech | 435/240 |

OTHER PUBLICATIONS

Guyton, A., Textbook of Medical Physiology, sixth edition, W. B. Saunders Co, Philadelphia, (1981), pp. 510–511, 338,339,844,845.
Isselbacher et al., (ed.), Harrison's Principles of Internal Medicine, ninth edition, McGraw-Hill Book Co (N.Y.) (1980), pp. 168–169, 1977–1979.
Nishiitsutsuji-Uwo et al., "Metabolic Activities of the Isolated Perfused Rat Kidney", Biochem. J., 103, 1967, pp. 852–862.
Wieland et al., "Interconversion of Pyruvate Dehydrogenase in Rats Heart Muscle upon Perfusion with Fatty Acids or Ketone Bodies", FEBS Letters, 1971, vol. 15, No. 4, pp. 295–298.
Dobrescu et al., "Relationship Between Glucose, Fatty Acid and Ketone Body Metabolism in Isolated Perfused Frog Heart," Rev. Roun. Bio.–Zoologie, vol. 18, No. 4, 1973, pp. 281–288.
Mayes et al., "Effect of Haematocki & Value and $pO_2$ on the Redox State and Metabolism it Perfused Liver", Biochem. J., vol. 156, 1976, pp. 685–689.
Menahan et al., "Regulation of Acetoacetyl-CoA in Isolated Perfused Rat Hearts", Eue. J. Biochem., vol. 119, 1981, pp. 295–299.

Primary Examiner—Esther M. Epplinger
Assistant Examiner—Carol A. Spiegel
Attorney, Agent, or Firm—Vogt & O'Donnell

[57] ABSTRACT

Living tissue lacking sufficient oxygenation due to conditions including anoxia and ischemia is treated with an aqueous solution containing acetoacetate in an amount sufficient for affording protection of the tissue from the effects of insufficient oxygenation. The solution may be in a form of an isotonic, hypertonic, perfusion, or cardioplegic solution and also may contain pyruvate and glycerol.

17 Claims, 2 Drawing Sheets

USE OF ACETOACETATE FOR PRESERVATION OF LIVING TISSUE

BACKGROUND OF THE INVENTION

This invention relates to the preservation of living tissue in the absence of oxygenation or in the event of insufficient oxygenation by the blood.

Under normal oxygenation conditions, reduction of the oxygen by the mitochondrial respiratory system supplies most of the energy emanating from the catabolism of the fatty acids and glucides in the form of adenosine triphosphate (ATP).

The reduction in the ATP and creatinine phosphate content of tissues which occurs in periods of non-oxygenation (anoxia) or insufficient irrigation (ischemia) by the blood promotes the development of irreversible cell changes during those periods and during reoxygenation of the tissues.

When the tissue is not irrigated and deprived of oxygen, the fermentation of glucose into lactate does supply some energy, but is accompanied by acidification of the cytoplasm of the cell due to the accumulation of lactate. This intracellular acidification impedes the metabolism and compromises the resumption of function of the tissue when irrigation and oxygenation resume.

The hypothesis has been put forward that, in certain animals, the metabolism under anaerobic conditions of aspartate and glutamate into succinate was linked to the non-oxidative phosphorylation of adenosine diphosphate (ADP) occurring inside the mitochondria (Hochachka, P., Owen, T.G., Amer. Zool. 13: 543–555, 1973).

On the other hand, the effect of intravenous infusion of glycerol monoacetoacetate as a non-protein energy source in burnt rats has been described and it has been shown that this compound can replace glucose as a source of energy during parenteral nutrition (Maiz, A., Moldawer, L.L., Bistrian, B.R., Biochem. J., 1985, 226/1, 43–50).

SUMMARY OF THE INVENTION AND DESCRIPTION OF PREFERRED EMBODIMENTS

Applicants have found that the addition of acetoacetate to a solution for perfusion of the heart under conditions of anoxia afforded protection against the functional changes resulting from the anoxia. This protective effect probably resulted from an anaerobic production of energy associated with the non-oxidative phosphorylation of ADP occurring in the mitochondria where the reduction of acetoacetate to $\beta$-hydroxybutyrate was coupled with the oxidation of other intra-cellular substrates into succinate. An effect such as this can also have a beneficial role in the preservation of other tissues than the heart, for example the kidneys, the liver or the eyes in the event of anoxia and ischemia.

Accordingly, the invention relates to the use of acetoacetic acid or one of its physiologically acceptable salts or esters for obtaining a pharmaceutical composition intended for the preservation of living tissues in the absence of oxygenation or in the event of insufficient oxygenation by the blood.

Physiologically acceptable salts or esters are understood to be the salts or esters which are normally encountered in perfusion or cardioplegic solutions. It is preferred to use sodium salts in an effective quantity for the desired protective effect.

The pharmaceutical composition advantageously also contains pyruvic acid or one of its physiologically acceptable salts or esters, preferably sodium pyruvate. It may also contain an energy-producing agent, for example glucose.

The pharmaceutical composition is advantageously formulated as a sterile isotonic or slightly hypertonic, physiological aqueous solution, for example a perfusion or cardioplegic solution of the type commonly used in operations on or transplantations of organs.

It is preferably used in situations where the organs are exposed to prolonged periods of anoxia or ischemia, for example during cardiac infarction or transplantation. Although the protective effect has been demonstrated in the case of the heart, there is no reason to assume that it would not be developed during operations on or transplantations of other organs, for example the eyes, the liver or the kidneys.

ILLUSTRATIVE DRAWINGS AND EXAMPLE

The invention is illustrated by the following Example which is preceded by a description of the perfusion system and the the method used for the various measurements of the cardiac function.

DETAILED DESCRIPTION OF THE DRAWINGS

Figure 1:
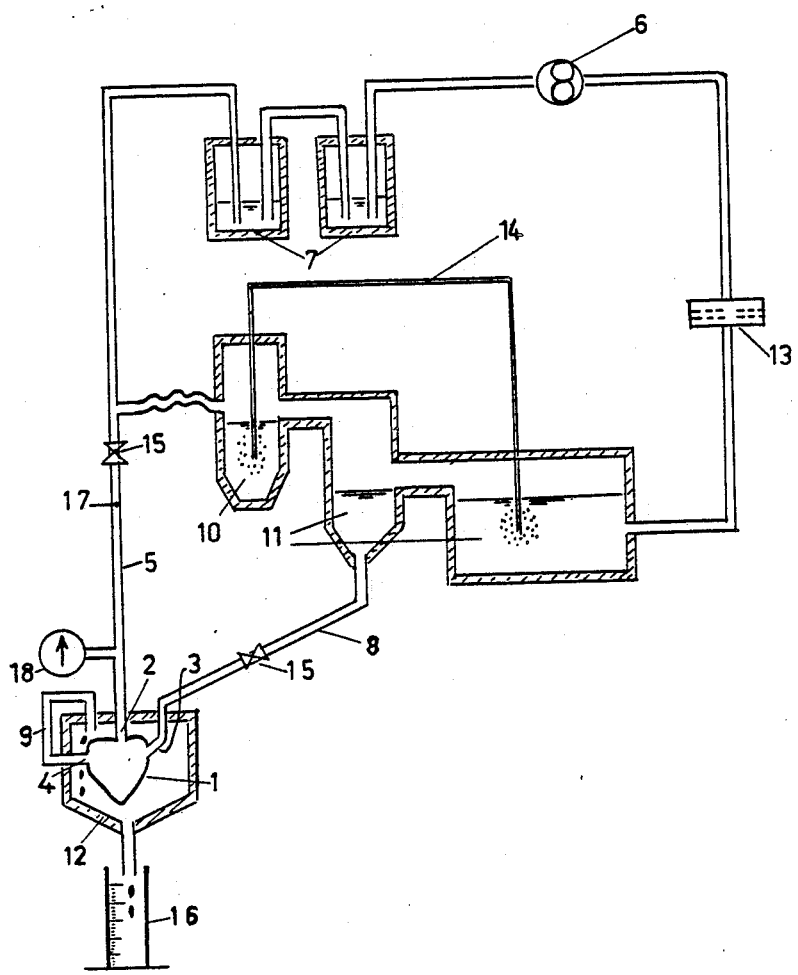
FIG. 1 is a schematic view of the perfusion system.

In FIG. 1, the heart 1 is cannulized by the aorta 2, the pulmonary veins 3 and the pulmonary artery 4. It is connected to the perfusion circuit by a cannula 5 of which one end is introduced into the aorta 2. The cannula 5 is itself connected at its other end to a peristaltic pump 6 (pulsed output) via thermostatically controlled double-walled reservoirs 7. Cannulas 8 and 9 respectively connect the pulmonary veins 3 to thermostatically controlled double-walled reservoirs 10,11 and the pulmonary artery 4 to a thermostatically controlled double-walled chamber 12 surrounding the heart. A cellulose acetate filter 13 (pore diameter 0.8 $\mu$m) placed between the reservoirs 11 and the pump 6 permanently clarifies the perfusion solution. The reservoirs 10,11 are provided with two circuits 14 for respectively supplying the perfusion liquid by bubbling with an oxygenated gas mixture (95%:$O_2$-5%:$CO_2$) and a nonoxygenated gas mixture (95%:$N_2$-5%:$CO_2$);

Valves 15 provide for immediate changeover from the retrograde perfusion technique, in which the heart 1 is perfused through the aorta 2 and does not expel liquid, to the anterograde or so-called "working heart" perfusion technique in which the heart is perfused through the pulmonary veins 3 and develops an aortic flow. In both techniques, it is possible to measure the coronary flow of the liquid which flows freely through the pulmonary artery 4 to the thermostatically controlled chamber 12 and is collected from there in a graduated cylinder 16. The pump 6 circulates the perfusion liquid and regulates the basic aortic pressure (post-charge). The filling pressure of the left ventricle (pre-charge) is regulated by vertical displacement of the reservoir 10 connected to cannula 8. In 17, the aortic pressure is measured by a pressure transductor (the pressure being calibrated by a mercury manometer 18), and the aortic flow is measured by an electromagnetic flowmeter with the aid of an intra-aortic probe.

Figure 2:
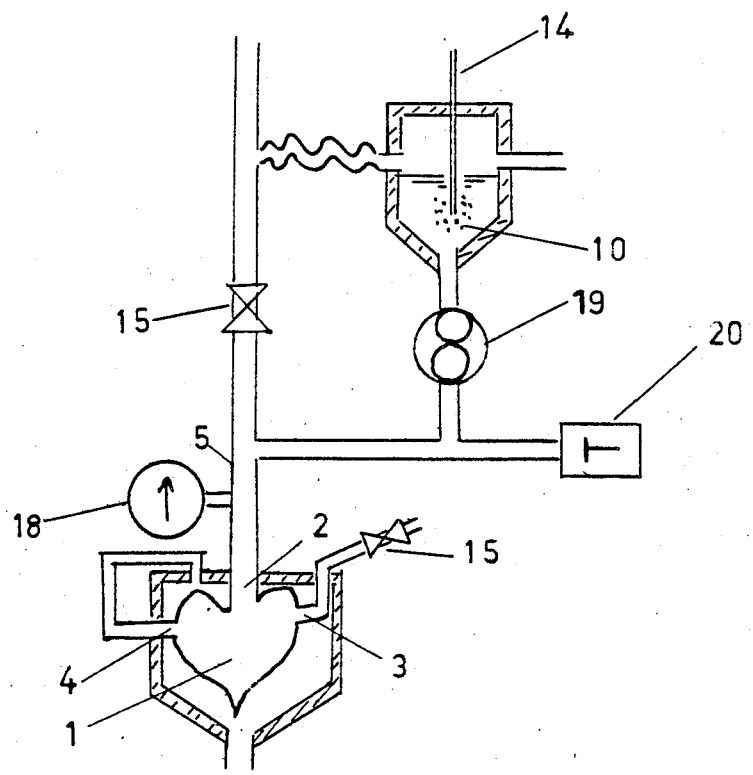
FIG. 2 shows a particular diagram of the perfusion system used solely during the anaerobic period.

In FIG. 2, an additional circuit segment connected to the non-oxygenated circuit comprises a pump 19 of constant and adjustable output by which the perfusion liquid can be circulated by the retrograde aortic route. The substances to be tested are introduced into the perfusion liquid at the level of the aorta by a miniature metering pump 20 of constant and adjustable output.

Perfusion method and measurements

The heart is taken from adult male Sprague-Dawley rats which have a body weight of from 250 to 320 g and which have been fed on a standard regime. The animals are mildly anaesthetized with ether and then decapitated. After excision, the heart is rapidly immersed in physsiological salt solution cooled to 4° C. which causes rapid cessation of the contractile activity. The perfusion period is divided into three phases.

Phase 1: aerobic stabilization period

The heart is rapidly connected to the perfusion system through the aorta and then perfused by the retrograde technique at a hydrostatic pressure of 7.8 kPa (60 mm Hg) which permits rinsing of the residual blood and resumption of the spontaneous beat. The pulmonary veins and the pulmonary artery are then connected up. The total duration of these two operations is 5 minutes. Perfusion is then changed over by means of the valves 15 to the anterograde technique using a liquid gassed with the oxygenated mixture which perfuses through the left atrium with a pre-charge of 1.6 kPa (160 mm $H_2O$)and a post-charge of 7.8 kPa (60 mm Hg). After a 15-minute stabilization period, the cardiac output (ml/min.) is measured, the cardiac output being the sum of the aortic and coronary outputs (liquid issuing from the chamber 12 coming from the pulmonary artery and losses through the apex of the heart).

Phase 2: anaerobic period

During this period which lasts 30 or 45 minutes, the heart is perfused through the aorta at a constant rate of 15 ml/min. with a perfusion liquid gassed with the non-oxygenated mixture. The solutions of substances to be treated are directly injected at the level of the aorta by the miniature pump 20 at a rate of 0.15 ml/min., the final molar concentration of these substances being 5 mM. After a few minutes of the anaerobic period, the contractile function of the heart stops completely.

Phase 3: aerobic recovery period

The heart is again perfused through the left atrium (anterograde technique) with a perfusion liquid gassed with the oxygenated mixture. The cardiac output and the aortic pressure are measured 15 and 30 minutes after reoxygenation of the perfusion liquid. They are expressed as a percentage of the values obtained before the anaerobic period.

Perfusion liquids

The stock perfusion liquid used is a bicarbonate buffer solution of the Krebs-Henseleit type brought to the temperature of 37° C. and consisting of: 120 mM NaCl, 5 mM KCl, 2.5 mM $CaCl_2$, 25 mM $NaHCO_3$, 1.2 mM $KH_2PO_4$, 1.2 mM $MgSO_4$ and 10 mM sodium pyruvate or sodium lactate.

The substances to be tested were prepared on the day of the test and their pH adjusted to 7.4 with NaOH. They were only added to the stock perfusion liquid during the anaerobic phase.

EXAMPLE 45 hearts were perfused with a stock perfusion liquid containing sodium pyruvate and 50 hearts with a stock perfusion liquid containing sodium lactate, after which the cardiac function parameters were measured at the end of phase 1 (aerobic period). The results obtained are shown in Table 1 below:

TABLE 1

|  | Stock continuous perfusion liquid containing | |
| --- | --- | --- |
|  | Pyruvate | Lactate |
| Weight of wet hearts (g) | 1.46 ± 0.03 | 1.39 ± 0.03 |
| Outputs (ml/min.) | | |
| Aortic | 19.1 ± 1.14 | 22.9 ± 1.1 |
| Coronary | 30.2 ± 1.3 | 27.3 ± 1.01 |
| Cardiac | 49.3 ± 1.46 | 50.2 ± 1.36 |
| Systolic aortic pressure (kPa) | 13.78 ± 0.25 | 14.25 ± 0.23 |

After an anaerobic period of 30 or 45 minutes (phase 2), during which some of the hearts were perfused with the solutions of substances indicated in Table 2 below, the functional recovery (phase 3) varied according to the nature of the substances supplied to the hearts during the anaerobic phase as shown in Table 2 below which indicates the proportion of hearts recovering a cardiac output after the anaerobic period.

TABLE 2

| Substrates | | Proportion of hearts recovering a cardiac output after an anaerobic period of | |
| --- | --- | --- | --- |
| stock continuous perfusion liquid containing | Solutions of substances to be tested perfused during the anaerobic period | 30 mins. | 45 mins. |
| Lactate | Lactate (control) | ⅛ | |
|  | Aspartate | 4/4 | 0/10 |
|  | Aspartate + glutamate + pyruvate* | ⅛ | |
| Pyruvate | Pyruvate (control) | 5/5 | 1/5 |
|  | Acetoacetate | 10/10 | 9/10 |
|  | Acetoacetate + glutamate* | 4/4 | 0/4 |
|  | β-hydroxybutyrate | ⅜ | 0/3 |

The aspartate, the glutamate, the pyruvate and the acetoacetate are in the form of the sodium salt.
*When there are several perfused substances (during the anaerobic period), they are successively introduced so that their final individual concentration is 5 mM.

Remarks

The majority of hearts in the control group receiving the lactate (stock perfusion liquid) did not recover measurable functions after reoxygenation. The addition of aspartate to the stock perfusion liquid provided for functional recovery of all the hearts examined after an anaerobic period of 30 minutes. The extra addition of glutamate appeared to interfere with the effect of the aspartate. In none of these groups was recovery observed after an anaerobic period of 45 minutes.

After an anaerobic period of 45 minutes in the presence of pyruvate (stock perfusion liquid), the proportion of hearts recovering a measurable output was significantly higher in the group receiving the acetoacetate than in the control group.

After an anaerobic period of 30 minutes, 95% of the hearts examined had recovered a measurable function.

However, better recovery of the cardiac contractility was already noticeable in the group receiving the acetoacetate. Thus, the aortic pressure was 69 ±3% of its value before the anaerobic period and the cardiac output 34 ±7% of its value before the anaerobic period for the control group. For the group receiving the acetoacetate, the aortic pressure was 76 ±3% of its value before the anaerobic period and the cardiac output 52 ±7% of its value before the anaerobic period.

The improvement in the tolerance by the heart of the anaerobic state produced by the acetoacetate was not enhanced but rather impaired by the addition of glutamate. In addition, the perfusion of β-hydroxybutyrate did not have a protective effect.

We claim:

1. A process for preserving living tissue comprising treating living tissue, wherein the living tissue has been removed from an organism and lacks sufficient oxygenation for preservation due to anoxia or ischemia, with an aqueous bicarbonate buffer solution which contains acetoacetate anions in an amount sufficient to afford protection of the tissue from the effects of insufficient oxygenation due to anoxia or ischaemia and which contains no hydroxybutyrate anions and no lactate anions.

2. A process according to claim 1 wherein the solution is prepared with compositions selected from the group consisting of acetoacetic acid, physiologically acceptable acetoacetate salts and physiologically acceptable acetoacetate esters.

3. A process according to claim 2 wherein the physiologically acceptable salt is sodium acetoacetate.

4. A process according to claim 1 wherein the solution further contains pyruvate anions.

5. A process according to claim 4 wherein the solution is prepared with compositions selected from the group consisting of pyruvic acid, physiologically acceptable pyruvate salts and physiologically acceptable pyruvate esters.

6. A process according to claim 5 wherein the physiologically acceptable salt is sodium pyruvate.

7. A process according to claim 1 or 4 wherein the solution further contains glucose.

8. A process according to claim 1 or 4 wherein the solution is selected from the group consisting of an isotonic solution, a hypertonic solution, a perfusion solution and a cardioplegic solution.

9. A process according to claim 7 wherein the solution is selected from the group consisting of an isotonic solution, a hypertonic solution, a perfusion solution and a cardioplegic solution.

10. A process according to claim 1 or 4 wherein the tissue is selected from the group consisting of heart, eye, liver and kidney tissue.

11. A process according to claim 1 or 4 wherein the solution contains an anaerobic gas.

12. A process for preserving organs removed from a living organism comprising perfusing an organ, wherein the organ lacks sufficient oxygenation for preservation due to anoxia or ischemia, with an aqueous bicarbonate buffer perfusion solution which contains acetoacetate anions in an amount sufficient to afford protection of tissue of the organ from the effects of insufficient oxygenation due to anoxia or ischaemia and which contains no hydroxybutyrate anions and no lactate anions.

13. A process according to claim 12 wherein the solution further contains pyruvate anions.

14. A process according to claim 12 or 13 further comprising first cooling the organ, then perfusing the organ with an aqueous solution for removing residual blood from the organ, next perfusing the organ with the solution, which contains the acetoacetate which is gassed with a non-aerobic gas and then perfusing the organ with an aerobically gassed aqueous solution for recovery of the organ.

15. A process according to claim 12 or 13 wherein the organ is heart.

16. A process according to claim 15 further comprising first cooling the heart, then perfusing the heart with an aqueous solution passed into the heart first by a retrograde technique and then by an anterograde technique, next perfusing the heart through its aorta with the solution which contains the acetoacetate gassed with a non-aerobic gas and then perfusing the heart with an aerobically gassed aqueous solution by an anterograde technique for recovery of the organ.

17. A process according to claim 12 or 13 wherein the organs are selected from the group consisting of eyes, livers and kidneys.

* * * * *